United States Patent [19]
Eisensmith et al.

[11] Patent Number: 5,553,477
[45] Date of Patent: Sep. 10, 1996

[54] PROGRESSIVE DIE APPARATUS AND METHOD FOR FORMING SURGICAL INCISION MEMBERS

[75] Inventors: Terry C. Eisensmith, Guilford, Conn.; Donald A. Morin, Goffstown, N.H.; George R. Proto, West Haven, Conn.

[73] Assignee: United States Surgical Corporation, Norwalk, Conn.

[21] Appl. No.: 320,015

[22] Filed: Oct. 7, 1994

[51] Int. Cl.⁶ .................................................. B21G 1/00
[52] U.S. Cl. ............................ 72/403; 72/415; 163/1; 163/5
[58] Field of Search ........................ 72/403, 399, 394, 72/415, 416; 163/1, 5

[56] References Cited

U.S. PATENT DOCUMENTS

| | | | |
|---|---|---|---|
| 3,253,328 | 5/1966 | Baldwin | 72/415 |
| 4,044,814 | 8/1977 | Zocher | 163/5 |
| 4,072,041 | 2/1978 | Hoffman | 163/5 |
| 4,799,311 | 1/1989 | Matsutani | 163/1 |
| 5,287,721 | 2/1994 | Samsel | 72/403 |
| 5,392,725 | 2/1995 | Takei | 163/5 |

FOREIGN PATENT DOCUMENTS

| | | | |
|---|---|---|---|
| 3824033 | 1/1990 | Germany | 163/5 |
| 458377 | 7/1950 | Italy | 163/5 |
| 63-309338 | 12/1988 | Japan . | |
| 3-230836 | 10/1991 | Japan . | |

Primary Examiner—Daniel C. Crane

[57] ABSTRACT

There is disclosed an apparatus for forming a surgical incision member comprising which includes a first die associated with a base and having a first groove therein for receipt of at least a portion of a needle blank. A second die is mounted for movement on the base between a position remote from the first die and a position adjacent the first die. The second die includes a second groove alignable with the first groove to hold a needle blank therebetween, the first and second dies each having spaced apart channels intersecting the first and second grooves. A notching die is provided and is mounted for movement within at the channels so as to engage and notch an edge of the needle blank contained within the first and second grooves. The apparatus also includes structure for curving a needle blank contained within the first and second grooves. A method of forming a surgical incision member is also disclosed, and a surgical incision member blank.

20 Claims, 10 Drawing Sheets

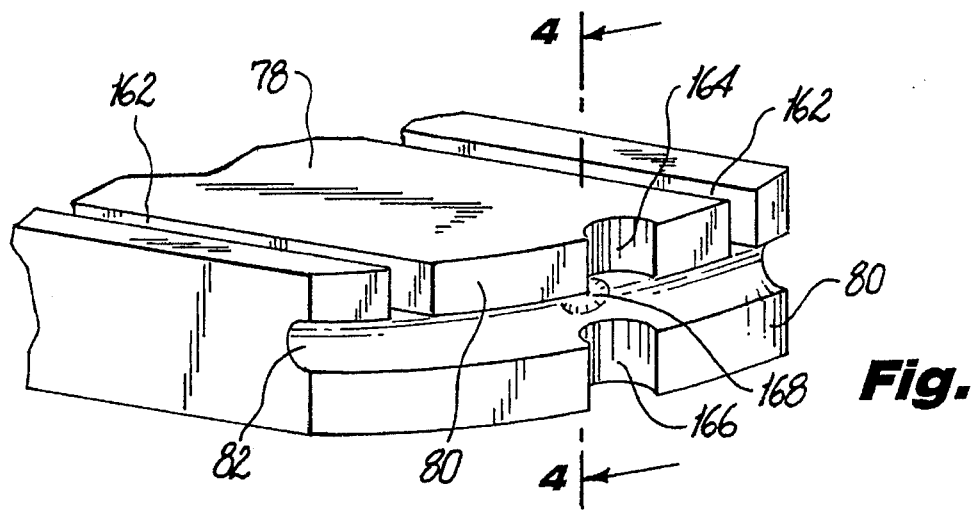
Fig. 3
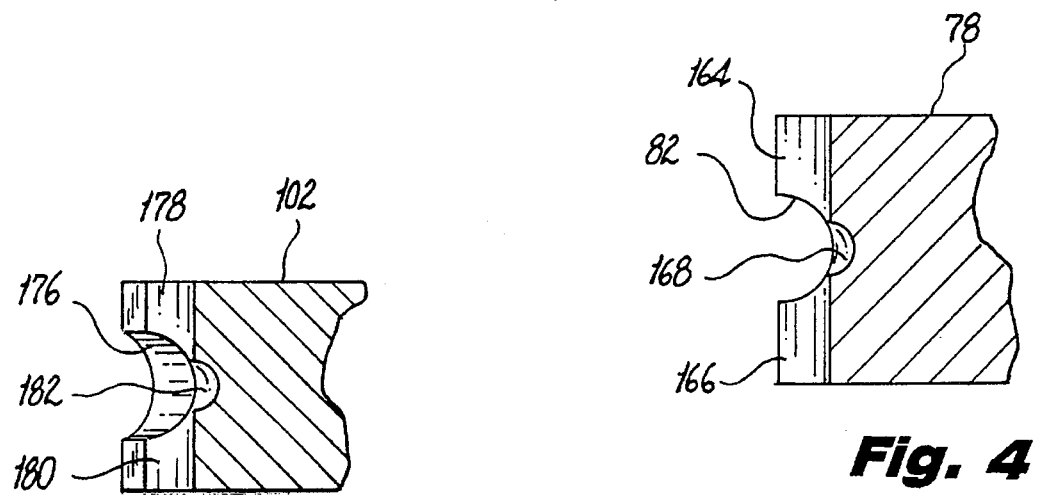
Fig. 4
Fig. 6
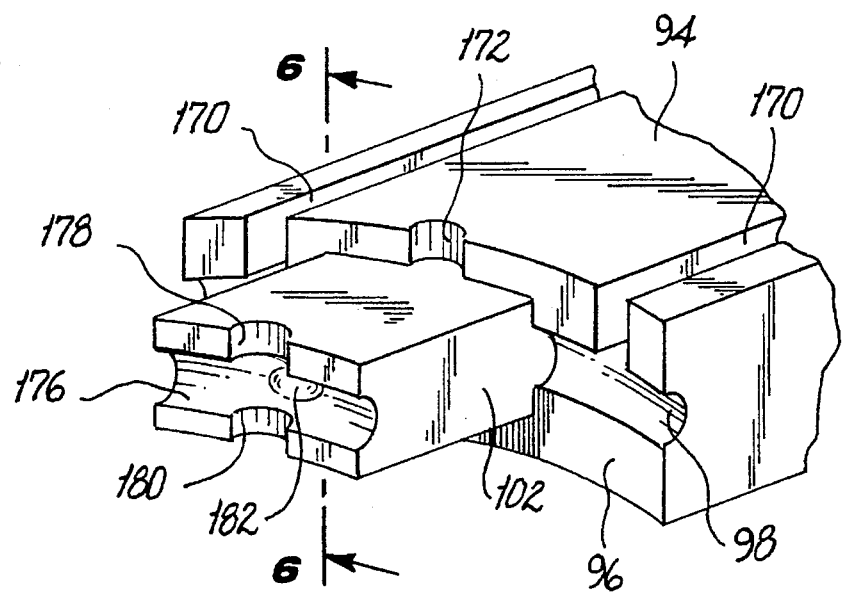
Fig. 5

PROGRESSIVE DIE APPARATUS AND METHOD FOR FORMING SURGICAL INCISION MEMBERS

BACKGROUND

1. Technical Field

This disclosure relates generally to surgical needle forming apparatus and, more particularly, to a progressive die apparatus and method for forming surgical incision member blanks from double pointed needle stock, and the resulting surgical incision member blank.

2. Description of Related Art

Surgical incision members are surgical grade suturing needles having points formed at one or both ends preferably include surgical suturing apparatus engagement structure formed within a body portion of the needle intermediate the pointed ends. Particular surgical incision members are disclosed in U.S. patent application Ser. Nos. 08/260,579, filed Jun. 16, 1994 entitled SURGICAL INCISION MEMBERS now allowed; 29/024,594, filed Jun. 16, 1994 entitled SURGICAL INCISION MEMBER; 07/954,013 filed Sep. 30, 1992 entitled SUTURING APPARATUS now abandoned; and 08/134,145 filed Oct. 8, 1993 entitled SURGICAL SUTURING APPARATUS WITH LOADING MECHANISM, now abandoned the disclosures of which are incorporated by reference herein. The suturing apparatus engagement structure is provided in the body portion of the surgical incision members to cooperate with corresponding engagement structure, such as, for example, needle engaging numbers or blades, on various surgical suturing apparatus. One particularly suitable apparatus for manipulation of surgical incision members is disclosed in U.S. patent application Ser. No. 08/134,145 filed Oct. 8, 1993 entitled SURGICAL SUTURING APPARATUS WITH LOADING MECHANISM. Apparatus engagement structure in the body portion of the needle blank along with cooperating engagement structure on the surgical suturing apparatus facilitates repeatedly passing the surgical incision member between a pair of arms or jaws in the suturing apparatus. In this manner the surgical suturing apparatus is able to securely and precisely control the surgical incision member for very effective, rapid and precise suturing of tissue. The apparatus engagement structure may be in the form of notches, holes, or crimps, etc., formed in the body portion of the surgical needle.

Additionally, surgical incision members may have various suture attachment structure formed in the body portion intermediate the pointed ends. Preferably, the suture attachment structure is positioned intermediate the apparatus engagement structure. The surgical incision members may be curved having a radius substantially equal to the distance between a pivot point and engagement structure on a pair of jaws. Alternatively, the surgical incision member may be relatively straight to facilitate transfer of the surgical incision member between a pair of parallel moving jaws or arms. The parallel moving arm or jaw structure may be in the form of arms or jaws which move perpendicular to each other axis or parallel to each other. One or both jaws of the suturing apparatus may move.

Due to the added manufacturing equipment necessary to produce apparatus engagement and suture attachment structure within the body portion of a needle, the manufacture of surgical incision members may often become complicated and costly. For example, one method of manufacturing the surgical incision member is by a process called metal injection molding or "MIM". The MIM manufacturing process tends to be very costly and thus may adversely affect the otherwise desirable characteristics and traits of a surgical suturing apparatus utilizing surgical incision members.

The production of needles in general involves many processes and different types of machinery in order to prepare quality needles from raw stock. These varying processes and machinery become more critical in the preparation of surgical grade needles where the environment of intended use is in humans or animals. Some of the processes involved in the production of surgical grade needles include, inter alia, straightening wire stock, cutting needle blanks from the wire stock, tapering or grinding points on one or both ends of the blank, and providing structure for receiving a suture thread at an end of the blank or at a location intermediate the ends. As used herein, the term "needle blank" refers to a piece of needle stock at various stages of completion but not fully formed into a surgical grade needle suitable for use during surgical procedures. Additionally, one skilled in the art will appreciate that flat surfaces may be formed on sides of the blank, typically by flat pressing portions of the needle blank to facilitate grasping by surgical instrumentation. Curving of the needle blank may also be performed where curved needles are desired. When providing curved needles for surgical procedures it is desirable for the needles to have a specified curvature, i.e., a predetermined radius of curvature. The desired radius of curvature for the finished needle varies with specific applications. Further, when surgical grade needles are made of steel or similar resilient materials, the curving anvil or mandrel used should have a smaller radius than the desired radius of the final surgical needle. This configuration allows for a "spring-back" or radial expansion effect after the curving operation to ensure that the desired radius of curvature is attained.

Surgical incision members typically require several processes to form the finished product. These processes may include curving and cutting needle stock to form needle blanks, altering or refining the tip configurations and curvature radius, punching or drilling the blank to form a suture hole and/or notching the blank to provide engaging structure for cooperative instrumentation.

Conventional needle processing is, in large part, a labor intensive operation requiring highly skilled labor and sophisticated machinery. One disadvantage to conventional needle processing is that most needle processing operations, such as, for example, cutting the blanks from stock, tapering the stock to form points, flat and side pressing of the body portion of the blanks, curving the blanks, notching, hole drilling, etc., are performed in batch operations on separate processing machines.

Thus, it would be desirable to have an apparatus for forming a large number of surgical incision members in a very short time and with a minimal amount of machinery. It would further be desirable to have an apparatus and a method of forming curved surgical incision members having a desired radius of curvature. It would be still further desirable to have an apparatus and a method of simultaneously imparting apparatus engagement structure and drill point guide holes in the body portion of a needle blank.

SUMMARY

The disclosed surgical incision member forming apparatus has a series of dies which are configured to progressively transform a straight, round bodied and double pointed needle blank into a surgical incision member. The apparatus generally includes a lower portion having a pair of spaced apart curving dies which are movable toward and away from each other to curve the needle blank therebetween and within a needle forming area of the apparatus. Feeding structure is provided to remove a needle blank from a reservoir of needle blanks and present them between the first and second curving dies. The lower portion also includes a dimpling die which is configured to engage an underside of the needle blank when held between the curving dies. The dimpling die imparts a dimple or pilot drill hole in an edge of the needle blank.

The upper portion of the apparatus has a series of camming mechanisms which are configured to sequentially move the first and second curving dies and the lower dimpling die. The camming members initially move the first and second curving dies to a position holding the needle blank and subsequently to a position to curve the needle blank therebetween. An additional camming member subsequently brings the lower dimpling die into engagement with the now curved needle blank.

The upper portion includes a notching and dimpling die with a pair of spaced apart notching blades and a dimpling pin positioned intermediate the blades. The notching and dimpling dies are affixed to the upper portion and are movable through spaced apart channels and a central bore within the first and second curving dies so as to engage an edge of the needle blank. The notching and upper dimpling dies are sequenced to engage the needle blank simultaneously with the engagement of the lower dimpling die in the lower portion.

There is also disclosed a method of forming a curved surgical incision member from a straight, round bodied and double pointed needle blank by holding a plurality of needle blanks within a storage member, transferring a single needle blank to a position between a pair of curving dies and curving the needle blank between the curving dies. The method further includes imparting apparatus engagement structure, in the form of engagement notches, to opposite ends of the needle blank and simultaneously dimpling opposite sides of the needle blank intermediate the apparatus engagement notches.

It is also contemplated that the needle blank could be formed of rectangular or square cross-section wire, or that the round bodied needle blanks could be side or flat pressed, as desired, to provide flat surface(s) on the needle.

There is also disclosed a surgical incision member needle blank.

BRIEF DESCRIPTION OF THE DRAWINGS

Various embodiments are described herein with reference to the drawings, wherein:

FIG. 3 is a perspective view of a convex curving die;

FIG. 4 is a partial cross-sectional view taken along line 4—4 of FIG. 3;

FIG. 5 is a perspective view of a concave curving die and positioning finger;

FIG. 6 is a cross-sectional view taken along the line 6—6 of FIG. 5;

DESCRIPTION OF PREFERRED EMBODIMENT(S)

Figure 1:
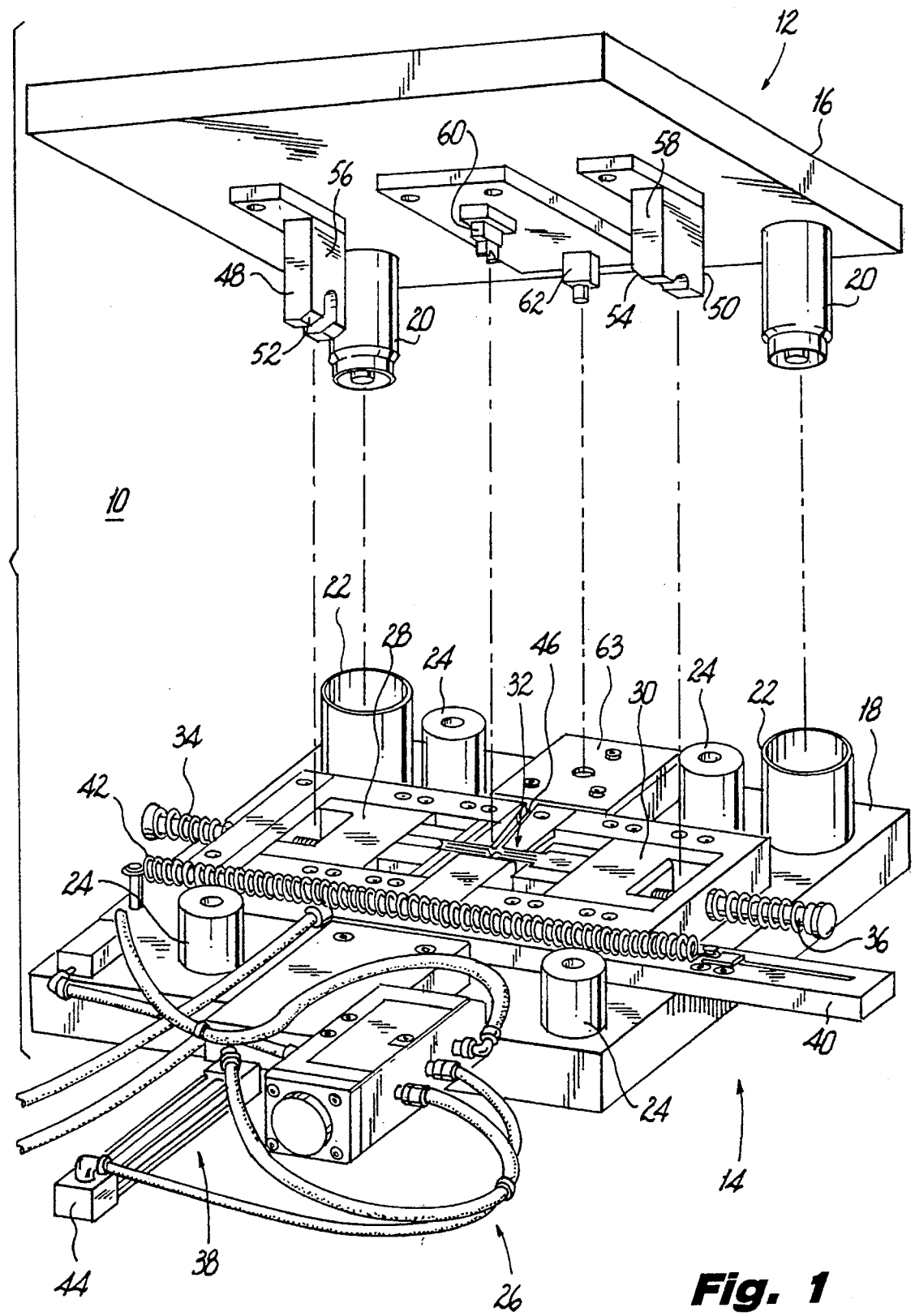
FIG. 1 is a perspective view of a progressive die apparatus for forming surgical incision members, with upper and lower portions separated.

Referring to FIG. 1, there is depicted a progressive die apparatus which is particularly suited to rapidly and precisely form a large number of surgical incision members. Apparatus 10 is designed to receive a straight, round bodied and double pointed needle blank such as, for example, needle blank 100 (FIGS. 2 and 7), and progressively curve and impart apparatus engagement structure into needle blank 100. Alternatively, apparatus 10 may also be modified to receive precurved needle blanks or, where straight surgical incision members are desired, dispense with the curving structure. Apparatus 10 also includes dies for forming guide holes or dimples intermediate the points and, preferably, on opposite sides of needle blank 100. These dimples serve to guide a drill point into engagement with needle blank 100 and to prevent burring on an opposite side of needle blank 100 as the drill point passes therethrough.

Apparatus 10 generally includes an upper portion 12 and a lower portion 14 which are movable relative to each other in a vertical direction. One skilled in the art will readily appreciate that other orientations of the components are also contemplated by this disclosure other than the relative vertical movement of upper and lower portions shown in this preferred embodiment.

Upper portion 12 includes an upper base plate 16 and lower portion 14 includes a lower base plate 18. Upper portion 12 generally includes structure for driving a series of die mechanisms located in lower portion 14. Apparatus 10 is, in part, operated by moving upper portion 12 in a vertical direction with respect to lower portion 14. A pair of movable hydraulic or air pressure cylinders 20, affixed to upper plate 16, are provided to move upper portion 12 in the vertical direction. Cylinders 20 are positionable within a pair of cylinder sleeves 22 affixed to lower plate 18 and movable therein. By varying the pressure in cylinders 20, upper plate 16 can be raised and lowered with respect to lower plate 18. Additionally, hydraulic apparatus (not shown) may be utilized to exert additional force on upper plate 16 in order to drive the various camming and die mechanisms.

Apparatus 10 further includes a system of air hoses 26 and a control block 27 which are utilized to pressurize cylinders 20 and operate a mechanism for feeding needle blanks through apparatus 10. A number of supports 24 on lower base plate 18 serve to limit the downward vertical motion of upper base plate 16.

Lower portion 14 generally includes first and second die mechanisms 28 and 30 which are mounted for movement with respect to lower plate 18 and each other. The various operations of curving needle blank 100, imparting apparatus engagement structure and dimpling of needle blank 100 all occur within a centrally located needle forming area 32. First and second die mechanisms, 28 and 30, respectively, may be reciprocated within needle forming area 32. A pair of springs 34 and 36 are provided to bias first and second die mechanisms 28 and 30, respectively, away from needle forming area 32.

A feeding mechanism 38 is provided to supply a plurality of needle blanks 100 and move a single needle blank 100 at a time into needle forming area 32. Feeding mechanism 38 generally includes a track or cartridge 40 suitable for containing a large number of needle blanks 100. Needle blanks 100 contained within cartridge 40 are biased by a spring 42 towards a pusher mechanism 44. Pusher mechanism 44 removes an individual needle blank 100 from cartridge 40 and moves it into needle forming area 32 for subsequent curving, notching and dimpling. Alternatively, various other methods of supplying a large number, or even continuous flow, of needle blanks 100 can be provided. These may include various hoppers, bowls, cartridges, etc. Needle holding cartridges, particularly of the cascade variety, can facilitate moving needle blanks 100 directly from a cutting and pointing apparatus (not shown) to apparatus 10. It is also contemplated that the needle blanks could be fed directly from a screw point cutting apparatus which cuts straight pointed needle blanks from wire stock.

Once needle blank 100 has been curved, notched and dimpled, it is ejected down an off-loading ramp 46 located on lower base plate 18 were it may be received within a suitable container for subsequent processing such as, for example, hole drilling and suture attachment.

In order to drive first and second die mechanisms 28 and 30, respectively, into and out of needle forming area 32 there are provided a pair of camming members 48 and 50 affixed to upper plate 16. First and second camming members 48 and 50 are of unequal length to sequentially move first and second die mechanisms, 28 and 30, and have respective camming surfaces 52 and 54 which are engagable with die mechanisms 28 and 30. Camming members 48 and 50 force camming die mechanisms 28 and 30 inwardly towards needle forming area 32 to curve and hold needle blank 100 positioned therein. Additionally, first and second camming members 48 and 50 each include dwell flats 56, 58 respectively to allow first and second die mechanisms 28 and 30 to securely hold a curved needle blank therebetween during subsequent notching and dimpling operations.

In order to impart the apparatus engagement structure and dimples in needle blanks 100, a notching and upper dimpling die 60 is provided affixed to upper plate 16. Upper plate 16 also includes a lower dimpling die camming member 62 which is utilized to drive a lower dimpling die 74 located beneath plate 18 (FIG. 2) into engagement with needle blank 100 simultaneously with the engagement of notching and upper dimpling die 60. Lower dimpling die camming member 62 drives lower dimpling die 74 through a lower die guide plate 63.

Figure 2:
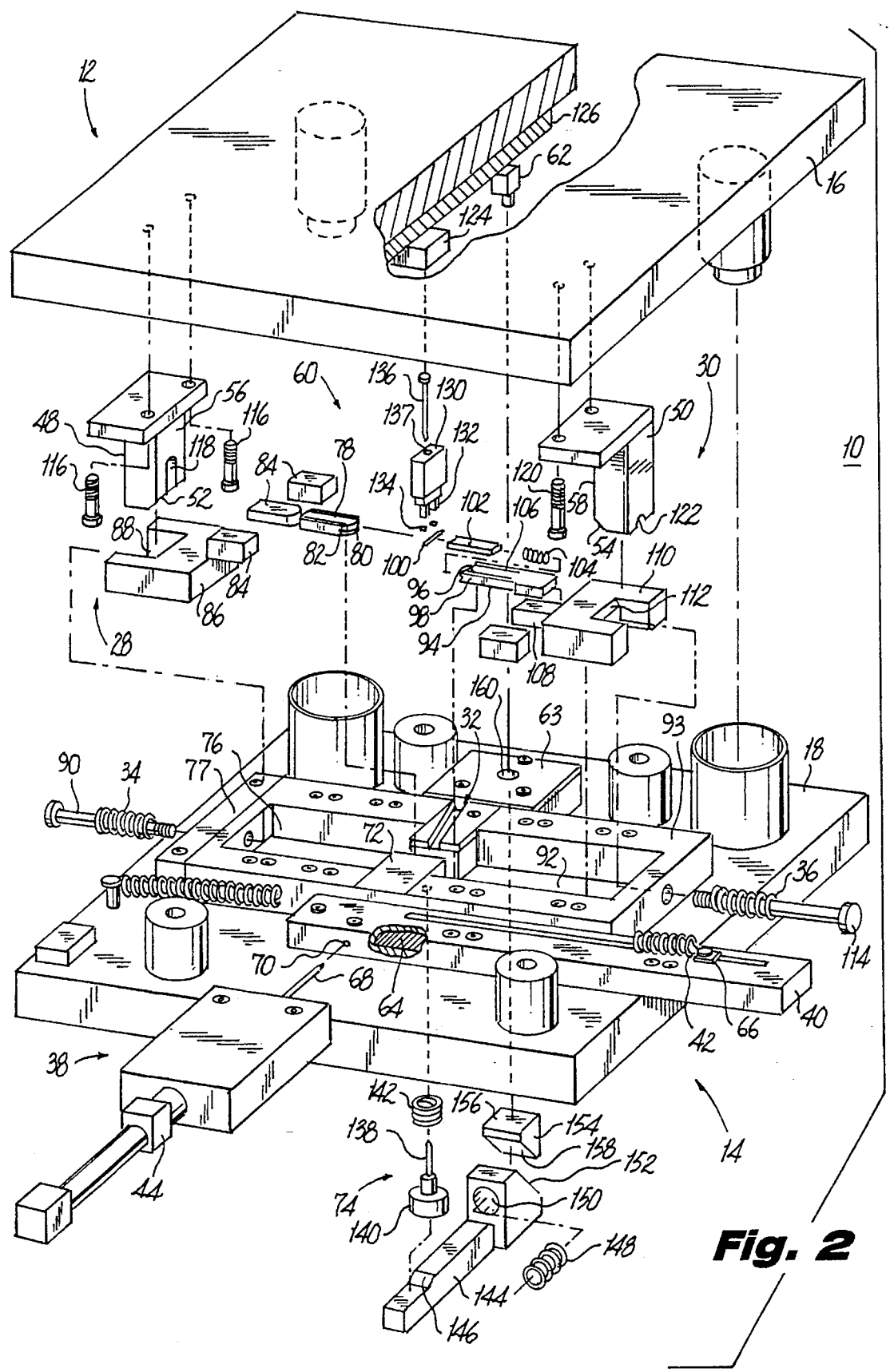
FIG. 2 is a perspective view of the apparatus of FIG. 1, with parts separated.
Figure 11:
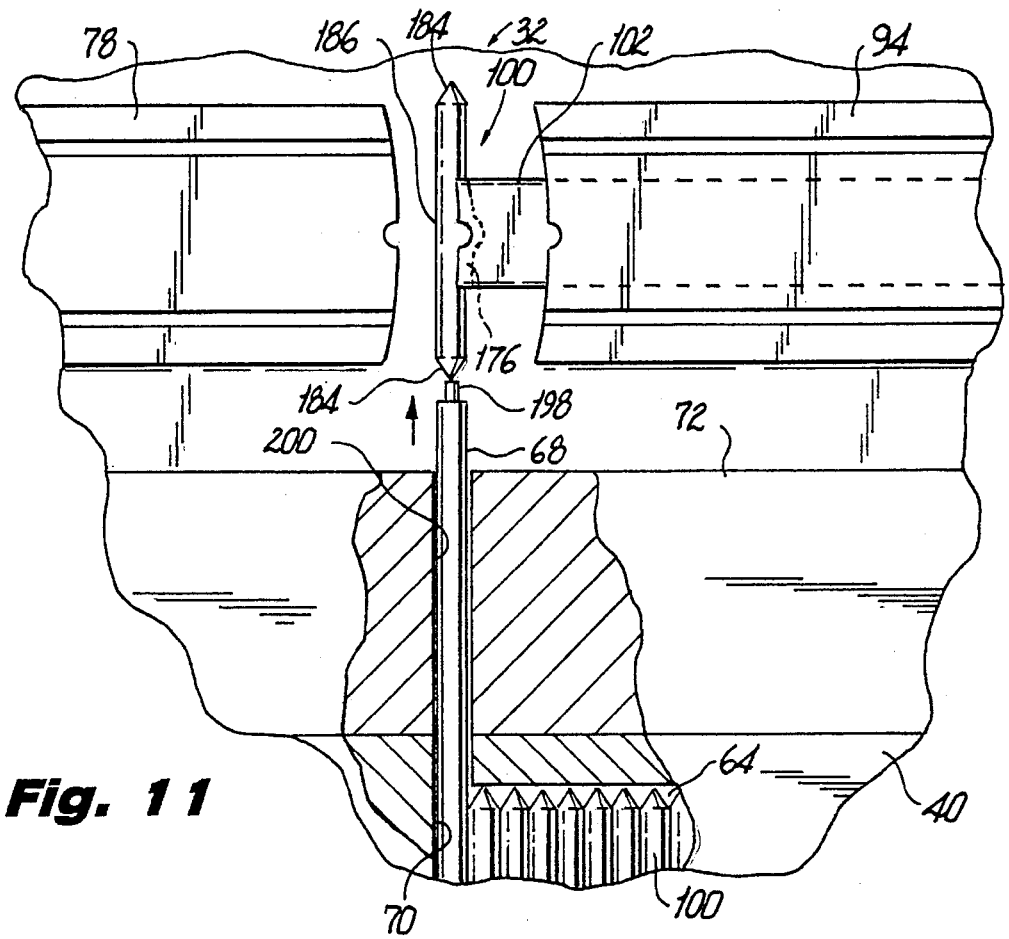
FIG. 11 is a top view, partially shown in section, of the needle blank being inserted in a needle forming area of the apparatus of FIG. 1.

A plurality of needle blanks 100 are contained within cartridge 40. Referring now to FIGS. 2 and 11, cartridge 40 includes an inner channel 64 which is configured to hold a plurality of needle blanks 100 in parallel arrangement. Feed mechanism 38 includes a spring puller 66 formed on spring 42 which serves to bias needle blanks 100 contained within channel 64 towards pusher mechanism 44.

Pusher mechanism 44 is provided to move needle blank 100 into needle forming area 33. Pusher mechanism 44 moves or picks off a needle blank from within channel 64 by means of a push rod 68. Push rod 68 is driven by air pressure through air hoses 26 (FIG. 1) and reciprocates within a load channel 70 formed in cartridge 40. As push rod 68 is repeatedly advanced, it removes a single needle blank 100 at a time from channel 64, at load channel 70, and funnels needle blank 100 through a channel block 72 to needle forming area 32 for processing (FIG. 11).

Apparatus 10 also includes lower dimpling die 74 which operates simultaneously with notching and upper dimpling die 60 to impart a pair of diametrically opposite dimples within a needle blank 100.

While notching and upper dimpling die 60 and lower dimpling die 74 move in a vertical direction, first and second die mechanisms 28 and 30 move in a horizontal direction on lower plate 18. First die mechanism 28 is located on lower plate 18 and is movably contained within a lower channel 76 defined by a series of guide supports 77. With reference to FIGS. 2 and 3, first die mechanism 28 generally includes a first curving die 78 having a needle curving or convex forming surface 80 formed thereon. Convex forming surface 80 has a radius slightly less than that of the desired surgical incision member radius to allow for springback of the needle blank material. A semi-circular groove 82 is formed within convex forming surface 80 to receive needle blank 100 therein and curve needle blank 100 without damage to the round cross-sectional area of the needle blank.

Should all or partial flat pressing also be desired, grooves 82 may have a configuration other than semi-circular. Additionally, where straight surgical incision members are desired, first curving die 78 may have a flat forming surface 80, in which case a needle blank 100 is merely held between first and second die mechanisms 28 and 30, respectively, for subsequent notching and dimpling. A series of guide blocks 84 are provided to guide first curving die 78 into engagement with needle blank 100 positioned within needle forming area 32.

Apparatus 10 includes a camming member 48 for driving first die mechanism 28 into needle forming area 32. Thus, first die mechanism 28 additionally includes a cam block 86 having a cam surface 88 which is engagable with cam surface 52 on camming member 48 (see, for example, FIG. 12a). Cam block 86 serves to drive first curving die 78 towards and hold first curving die 78 against needle blank 100 in response to a lowering of camming member 48. Spring 34 is provided to bias first die mechanism 28 away from needle forming station 32. Thus, there is also provided a biasing rod 90 which is insertable within spring 34 and engages cam block 86 to draw cam block 86, and thus first curving die 78, away from needle forming area 32 in the absence of camming member 48.

Referring to FIGS. 2 and 5, second die mechanism 30 is located on lower plate 18 generally opposite first die mechanism 28. As with first die mechanism 28, second die mechanism 30 is movably disposed within a guide channel 92 defined by a series of guide supports 93. Second die mechanism 30 generally includes a second curving die 94 which has a generally concave forming surface 96 of predetermined radius. Concave forming surface 96 cooperates with convex forming surface 80 of first curving die 78 to curve straight needle blank 100 positioned therebetween. To prevent deformation to the cross-sectional area of the needle blank 100 to be curved, concave surface 96 also includes a semi-circular needle groove 98 formed therein.

To facilitate receipt of needle blank 100 from feed mechanism 38, a positioning finger 102 is provided and is slidably disposed within a finger channel 106 formed in second curving die 94. Positioning finger 102 is generally biased into an extended position away from concave forming surface 96 of second curving die 94 by means of a spring 104 in second curving die 94.

Second die mechanism 30 also includes a series of guide blocks 108 to guide second curving die 94 into engagement with needle blank 100. Second die mechanism 30 further includes a cam block 110 having a camming surface 112. Similar to cam block 96 described hereinabove, cam block 110 is provided to move second curving die 94 toward needle forming area 32, and thus into engagement with needle blank 100, in response to downward vertical movement of camming member 50. Camming surface 54 on camming member 50 engages camming surface 112 on cam block 110 to thereby drive die 94 into engagement with needle blank 100. Further, camming mechanism 38 additionally includes a biasing rod 114 which is movably mounted within spring 36 and attached to cam block 110 in order to bias second die mechanism 30 away from needle forming area 32.

First upper camming member 48 is positively affixed to upper plate 16 by a pair of bolts 116. Further, upper camming member 48 generally includes a rod clearance channel 118 which straddles and provides clearance for biasing rod 90 as upper plate 16 moves down toward lower plate 18. Similarly, second upper camming member 50 is also affixed to upper plate 16 by means of bolts 120 and additionally includes a rod clearance channel 122 to provide clearance for biasing rod 114.

Referring to FIGS. 2 and 7–10, in addition to curving needle blank 100, when forming a surgical incision member, apparatus engagement structure, preferably in the form of notches, must be formed in the body of needle blank 100. It also is preferable to provide dimples intermediate the apparatus engagement structure for later hole drilling and subsequent suture attachment. Thus, notching and upper dimpling die 60 is sequenced to engage needle blank 100 after having been curved by first and second curving dies 78 and 94, respectively.

Notching and upper dimpling die 60 is affixed to upper base plate 16 by means of a block 124 and an upper plate 126 and moves in the vertical direction with upper base plate 16. Notching and upper dimpling die 60 generally includes a die fixture 130 having a pair of spaced apart blades 132 extending downwardly therefrom. Blades 132 are provided to secure a pair of notching dies 134 and bring them into engagement with opposed ends of needle blank 100 to impart apparatus engagement structure therein. Preferably, blades 132 are removable from die fixture 130 for replacement and to alter the distance between blades 132 and thus between notching dies 134. Further, upper dimpling die 136 is removably mounted within a bore 137 in fixture 130 at a position intermediate blades 132. Thus, upon stamping with notching and upper dimpling die 60, a dimple is imparted to needle blank 100 intermediate the notches imparted by notching dies 134.

Figure 10:
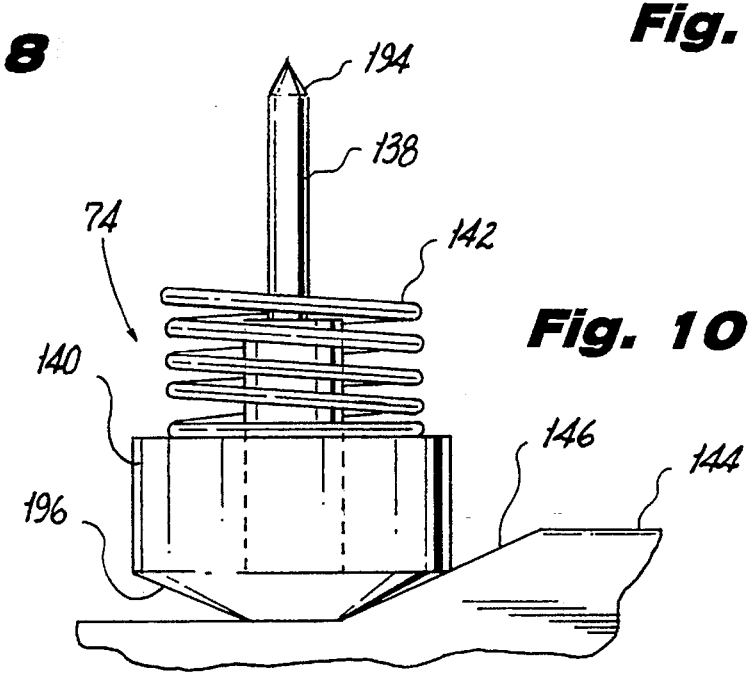
FIG. 10 is a side view of a lower dimpling die.

Lower dimpling die 74 is sequenced for engagement with needle blank 100 simultaneously with the engagement of notching and upper dimpling die 60. As shown in FIGS. 2 and 10, lower dimpling die 74 generally includes a pointed lower dimpling die rod 138 affixed to a base member 140. Lower dimpling die rod 138 is biased away from needle forming station 32 by means of a spring 142. In order to move base member 140 and dimpling die rod 138, up to needle forming area 32, there is provided a drive member 144 having a first camming surface 146 which is engagable with base member 140. Drive member 144 is slidable in a horizontal direction in response to movement of lower dimpling die camming member 62. Preferably, first camming surface 146 is biased away from base member 140 by means of a spring 148 positioned within a bore 150. Drive member 144 additionally includes a second camming surface 152 which is engagable with a transfer block 154. Transfer block 154 includes an upper camming edge 156 which receives pressure from lower dimpling die camming member 62 and a transfer block camming surface 158 which is engagable with second camming surface 152 to thereby move drive member 144 in response to a lowering of lower dimpling die camming member 62. As noted hereinabove, lower dimpling die camming member 62 is guided by guide plate 63 and passes through a bore 160 within guide plate 63.

First curving die 78 is shown in detail in FIG. 3 and includes groove 82 to hold and impart an arcuate profile to a needle blank 100. In addition to groove 82, first curving die 78 includes a pair of longitudinally aligned slots 162 which intersect needle curving groove 82. Slots 162 provide clearance for blades 132 and notching dies 134 to allow notching dies 134 to impact needle blank 100 contained within groove 82. First curving die 78 additionally includes an upper bore 164 to allow upper dimpling die 136 to engage needle blank 100 and a lower bore 166 to allow lower dimpling die rod 138 to engage needle blank 100.

Upper and lower dimpling dies 136 and 74 are provided to punch a drill guiding dimple in one side of a needle blank 100 and a burr preventing dimple in the opposite side of needle blank 100. The dimples will be utilized in a later stage to allow a suture hole to be drilled through needle blank 100. Preferably, dimpling dies 136 and 74 form a dimple having an angle of approximately 120 degrees in the sides of needle blank 100. Once needle blank 100 has been drilled with a suture hole, it is desirable to crimp a suture within needle blank 100.

A preferred method of providing structure for subsequent crimping of a suture is best shown in FIG. 4, where first curving die 78 includes a bulge recess 168 formed within curving groove 82. Bulge recess 168 allows expansion of needle stock material therein when needle blank 100 is impacted with dimpling dies 136 and 138. The deformation in needle stock material forms bulges on the outside of needle block 100 which, when a length of suture material is to be crimped within needle blank 100, are crimped or compressed back flush with a body portion of needle blank 100 to force material inwardly in the drilled hole and thereby capture the length of suture material.

As shown in FIG. 5, second curving die 94 also includes slots 170 similar to slots 162 described hereinabove. Further, second curving die 94 also includes an upper bore 172 for receipt of upper dimpling die 136 and a lower bore 174 (FIG. 15) for receipt of lower dimpling die 138.

In order to form the curvature in needle blank 100 and provide access for dimpling dies 136 and 138 when second curving die 94 is advanced against first curving die 78, positioning finger 102 is formed with a needle receiving groove 176 and a pair of upper and lower dimpling die receiving bores 178 and 180, respectively. Additionally, similar to first curving die 78, positioning finger 102 also includes a bulge recess 182 formed within groove 176. As shown in FIG. 6, bulge recess 182 allows expansion of needle blank material therein to form a crimping bulge in the body portion of the needle blank.

It will be noted that when positioning finger 102 has been driven fully within second curving die 94, upper dimpling die bore 178 and lower dimpling die bore 180 are in alignment with upper dimpling die bore 172 and lower dimpling die 174 in second curving die 94. Similarly, needle receiving groove 176 is alignment with needle receiving groove 98.

Figure 7:
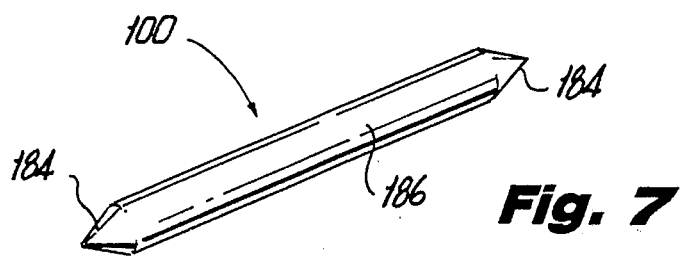
FIG. 7 is a perspective view of a straight, round bodied needle blank having points at either end.
Figure 8:
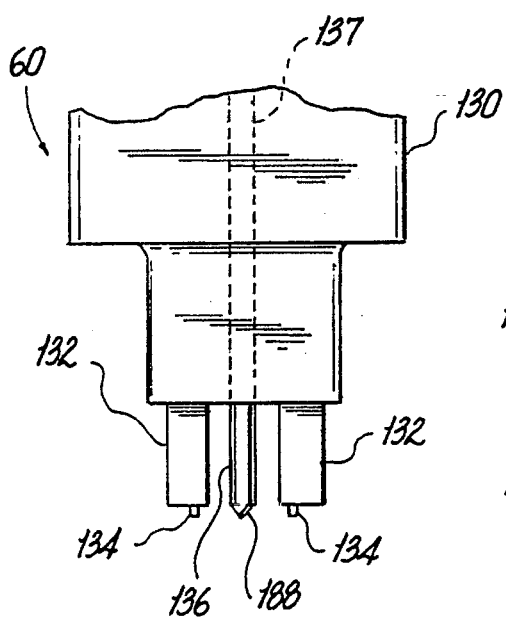
FIG. 8 is side view of a notching and upper dimpling die.
Figure 9:
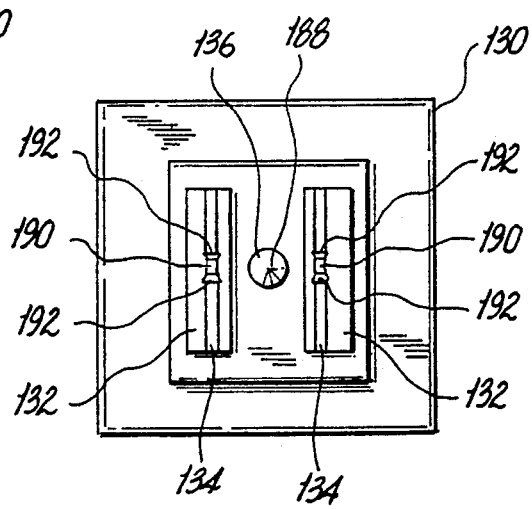
FIG. 9 is an end view of the notching and upper dimpling die.

Turning now to FIG. 7, there is shown a suitable needle blank 100 for use within progressive die apparatus 10. Needle blank 100 includes points 184 at either end and a relatively straight body portion 186. Needle blank 100 is preferably formed on a screw thread cutting apparatus which takes a coil or length of wire needle stock and passes it between single thread cutting dies to cut points in the ends of a needle blank. Referring to FIGS. 8 and 9, notching dies 134 include a configuration particularly suited to imparting a flared end notch within body portion 186 a of needle blank 100. Thus, dies 134 include a relatively parallel notching or center die portion 190 having flared ends 192. Flared ends 192 provide suitable clearance or lead in tapers in body portion 186 of needle blank 100 to allow a blade or other engagement type structure on a suturing apparatus to engage the notches formed in the needle blank 100.

In addition to notching dies 134, notching and upper dimpling die 60 includes a dimpling point 188 formed on an end of upper dimpling die 136.

Lower dimpling die 74 is sequenced to impact needle blank 100 simultaneously with notching and upper dimpling die 60. Referring to FIG. 10, lower dimpling die pin 138 includes a pointed dimpling die point 194. To drive dimpling die 74 upwardly against the bias of spring 142, an angled camming surface 196 provided on cam base 140. Thus, as drive member 144 is advanced against lower dimpling die 74, first cam face 146 engages angled camming face 196 thereby driving lower dimpling die 74 upwardly against the bias of spring 142.

The operation of apparatus 10 to form a surgical incision member from needle blank 100 will now be described with reference to the die operations and their corresponding respective actuating camming member positions shown in elevation. Beginning with FIG. 11, and as noted hereinabove, feeding mechanism 38 is provided to take a single needle blank 100 at a time off of cartridge 40 and move it into needle forming area 32. To engage needle blank 100, push rod 68 is reciprocated toward needle forming station 32. As push rod 68 passes through load channel 70, a distal end 198 of push rod 68 moves needle blank 100 through load channel 70 and out of inner channel 64. Needle blank 100 is then driven longitudinal through a channel 200 formed in channel block 72. Push rod 68 preferably has a diameter substantially equal to that of needle blank 100. Push rod 68 moves needle blank 100 to a position intermediate first curving die 78 and second curving die 94 such that body portion 186 of needle blank 100 enters into and is supported by needle groove 176 in positioning finger 102. In this manner a single needle blank at a time is removed from cartridge 40 and moved into needle forming area 32 for processing.

Figure 11A:
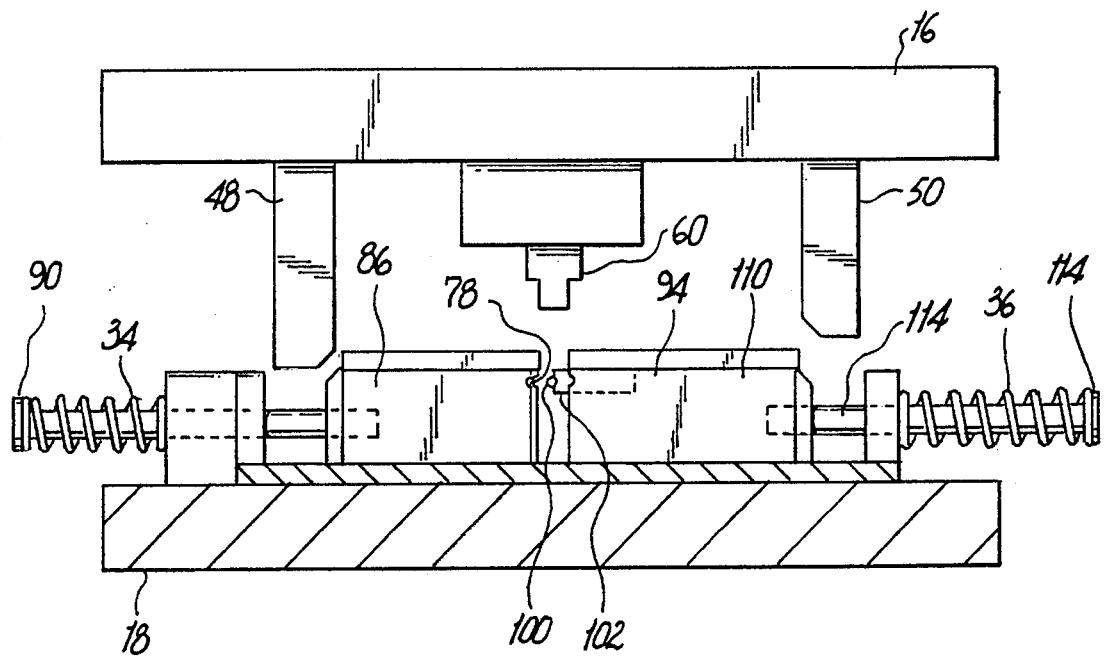
FIG. 11A is a side elevational view illustrating camming member and die positions corresponding to FIG. 11.

In the loading stage, plate 16 is at its highest position above plate 18 and is stationary (FIG. 11A). Camming members 48 and 50 are positioned remote from respective cam blocks 86 and 110. Notching and upper dimpling die 60 is positioned remote from needle forming area 32. Springs 34 and 36, by means of biasing rods 90 and 114, bias cam blocks 86 and 110, and thus first and second curving dies 78 and 94, respectively, into a retracted most position.

Figure 12:
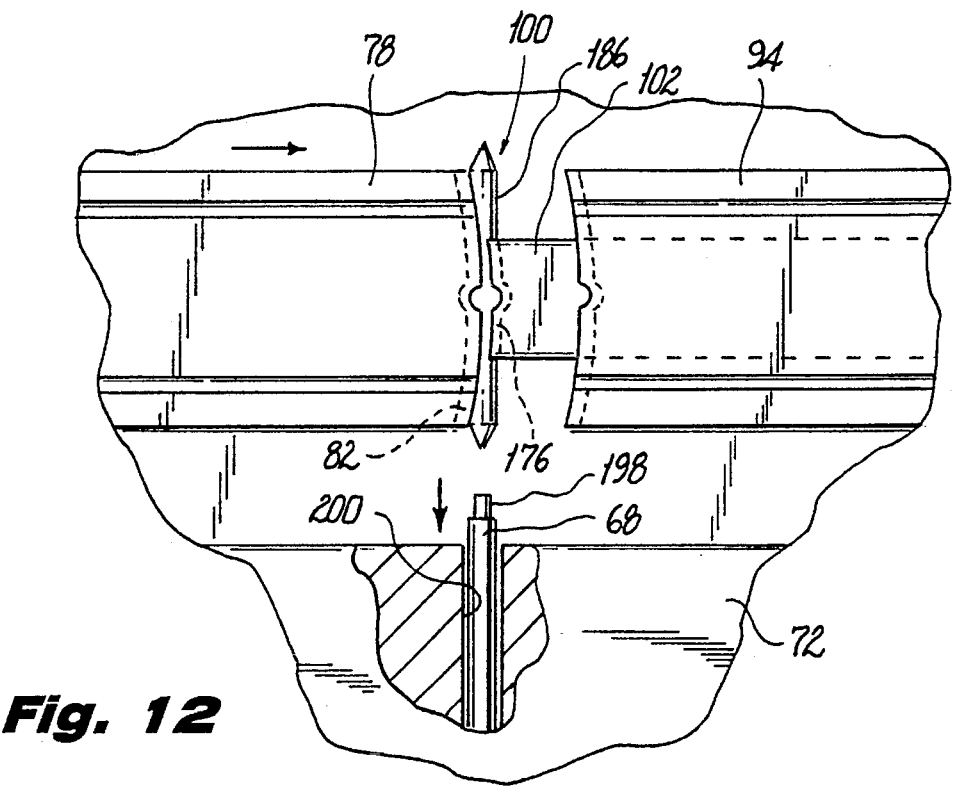
FIG. 12 is a top view, partially shown in section, showing the needle blank being captured between the convex curving die and the positioning finger.
Figure 12A:
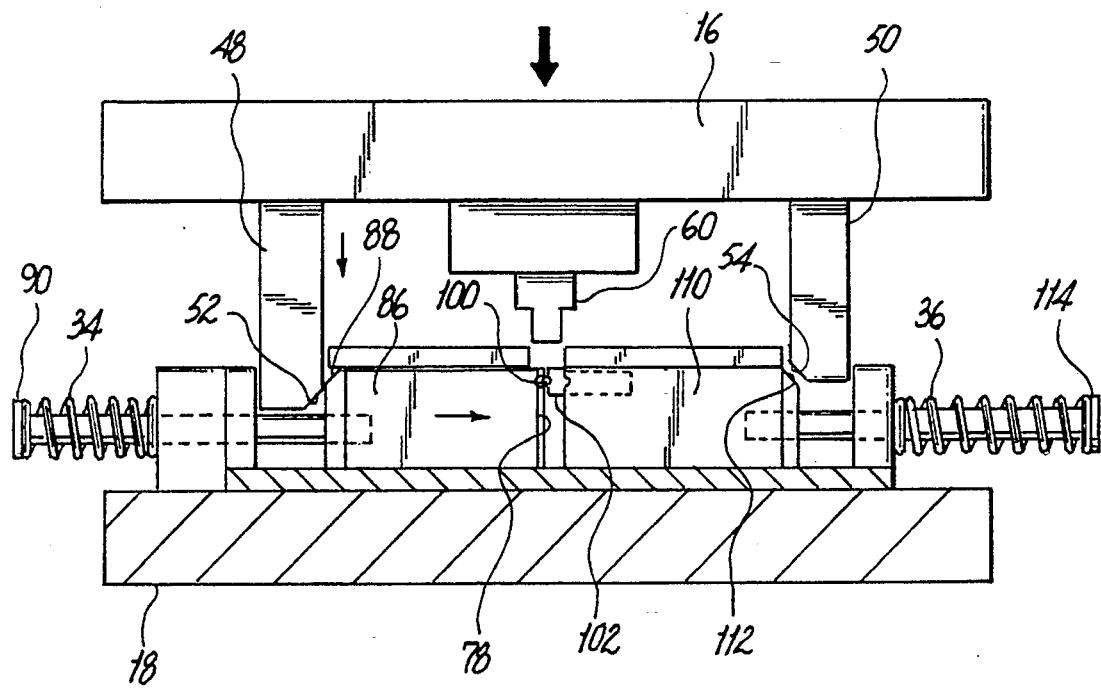
FIG. 12A is a side elevational view illustrating camming member and die positions corresponding to FIG. 12.

To form needle blank 100 into a surgical incision member, driving cylinders 20 are operated to move downwardly within sleeves 22 thereby lowering upper base plate 16 relative to lower base plate 18 (FIG. 12A). As upper base plate 16 moves downwardly, camming surface 52 on camming member 48 engages camming surface 88 on cam block 86 thereby driving cam block 86 into an advanced position towards needle blank 100. As cam block 86 advances toward needle blank 100, it draws with it biasing rod 90 thereby compressing spring 34. As shown, camming surface 54 of second camming member 50 remains disassociated from angled camming surface 112 on cam block 110.

Referring now to FIG. 12, as cam block 86, and thus first curving die 78, moves into an advanced position, needle blank 100 enters into groove 82 thereby holding needle blank 100 between first curving die 78 and groove 176 in positioning finger 102. Simultaneously with the capture of needle blank 100 between first curving die 78 and positioning finger 102, push rod 68 is retracted back within channel 200 to a position where, upon completion of a forming operation, it may again cycle to pick up another needle block 100 and advance it into needle forming area 32. At this point needle blank 100 is suspended between first curving die 78 and positioning finger 102. Alternatively, first curving die 78 can be positioned as shown in FIG. 12 prior to advancing needle blank 100. In this case, push rod 68 would place needle blank 100 directly between die 78 and finger 102.

Figure 13:
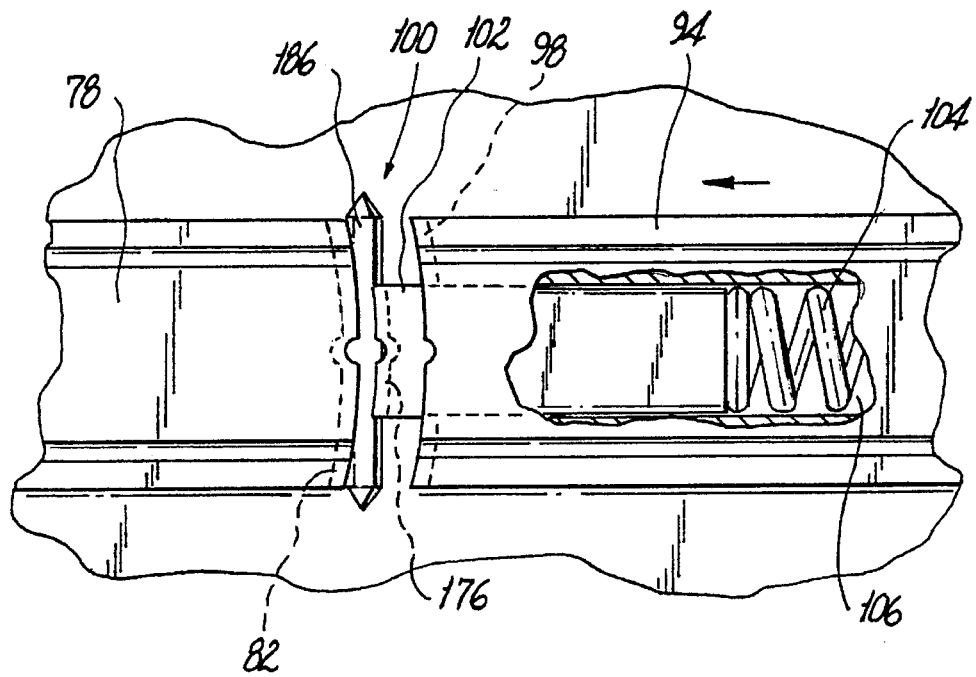
FIG. 13 is a top view partially shown in section of the concave curving die initiating the curving sequence.
Figure 13A:
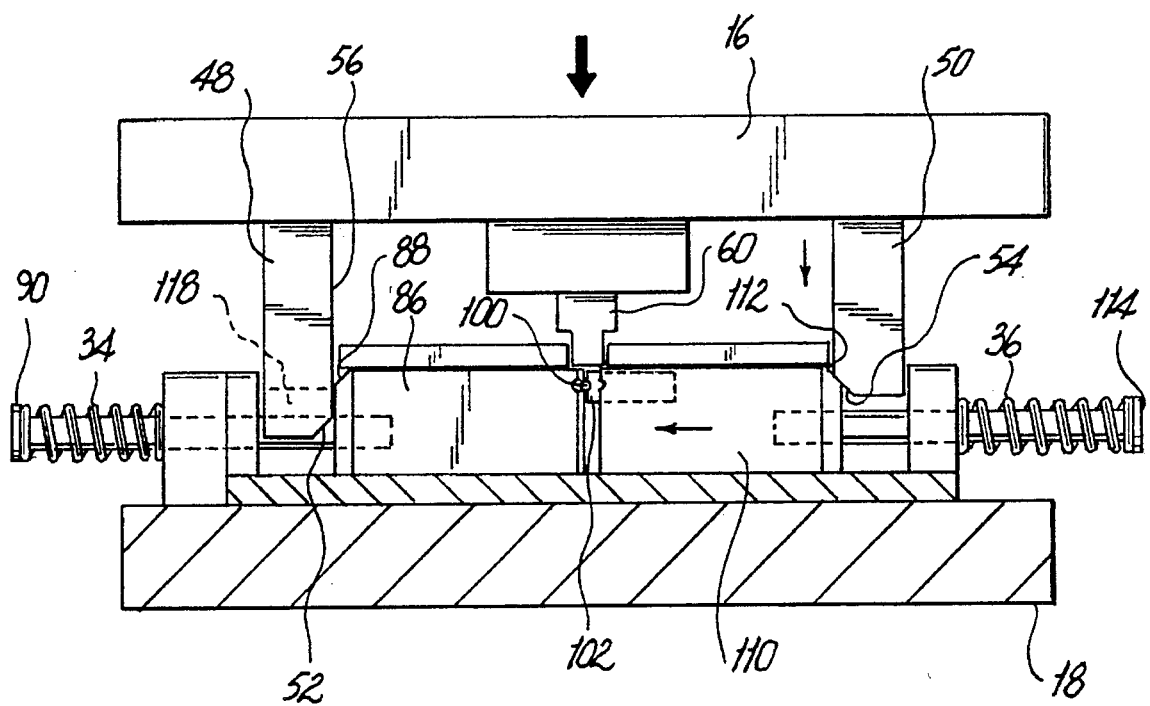
FIG. 13A is a side elevational view illustrating camming member and die positions corresponding to FIG. 13.

In FIGS. 13 and 13A, as upper base plate 16 is lowered further, camming surface 52 on camming member 48 clears camming surface 88 on cam block 86 as shown in FIG. 13A. Dwell flat 56 of cam member 48 slides along cam block 86 thereby locking cam block 86 into position and preventing any further movement thereof. Additionally, as camming member 48 moves downwardly, rod clearance channel 118 straddles biasing rod 90 to allow upper base plate 16 to move further downward, and continue the needle forming process. As shown, angled camming surface 54 of camming member 50 engages camming surface 112 of cam block 110 to advance cam block 110, and thus second curving die 94, towards the now suspended needle cam block 100. Advancement of cam block 110 draws with it biasing rod 114 which compresses spring 36.

As second curving die 94 is advanced towards now stationary first curving die 78, positioning finger 102 is forced rearwardly within channel 106 thereby compressing spring 104. Further, groove 98 in second curving die 94 advances towards body portion 186 of needle blank 100.

Figure 14:
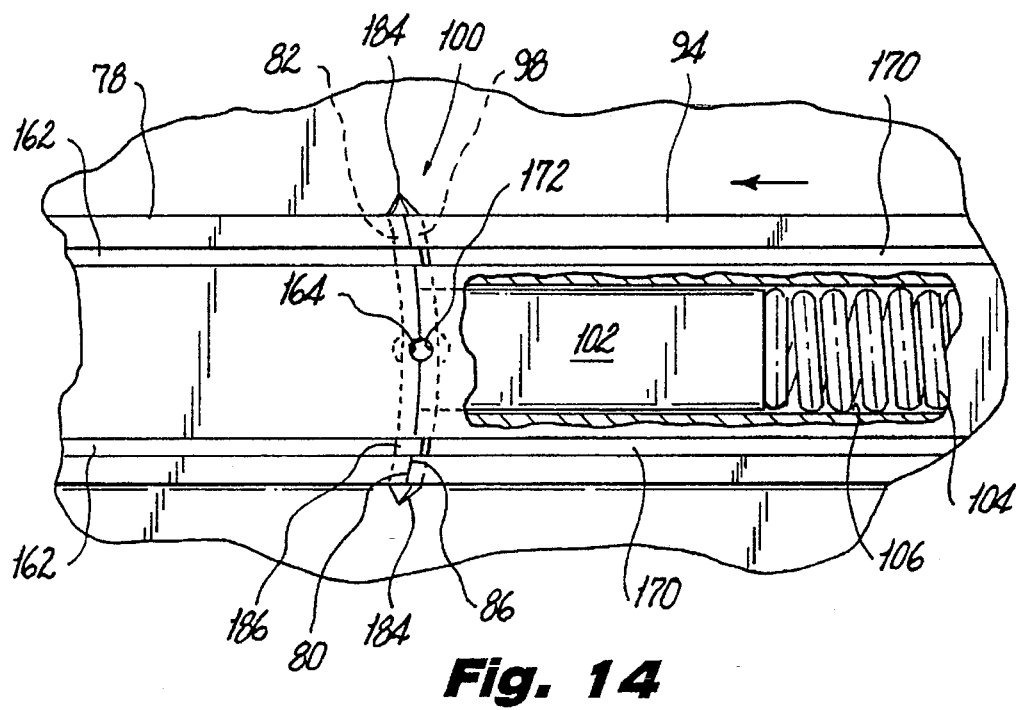
FIG. 14 is a top view, partially shown in section, illustrating the needle blank being curved between the convex and concave curving dies.
Figure 14A:
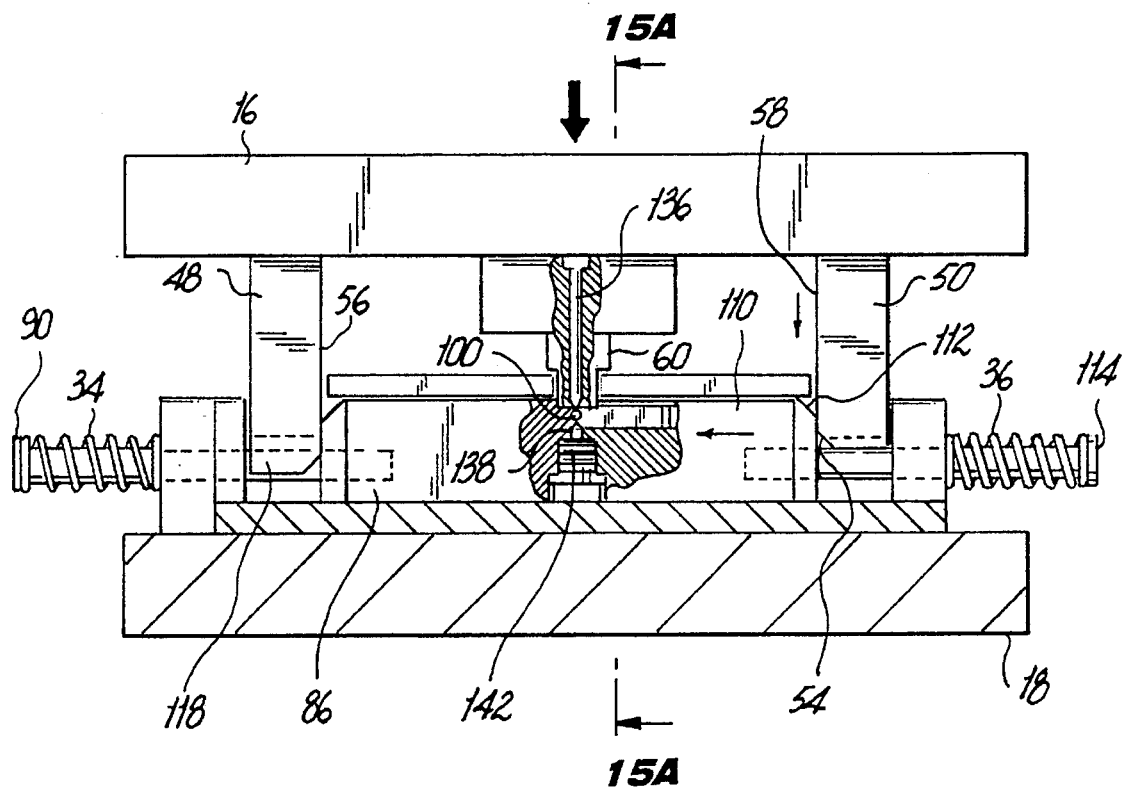
FIG. 14A is a side elevational view, partially shown in section, illustrating camming member and die positions corresponding to FIG. 14.

To complete the curving sequence, upper base plate 16 is lowered further (FIGS. 14 and 14A). Rod clearance channel 118 in camming member 48 moves further down around biasing rod 90. Camming surface 54 on camming member 50 clears camming surface 112 on cam block 110 and allows a dwell flat 58 to engage cam block 110. Thus, upon complete advancement of second curving die 94 towards first curving die 78, body portion 186 of needle blank 100 is curved between first curving die 78 and second curving die 94. Finger 102 is forced into a retracted most position within channel 106 compressing spring 104 further.

As camming members 48 and 50 enter dwell positions, convex forming surface 80 abuts concave forming surface 86. Upper dimpling die bore 164 in first curving die 78 aligns with upper dimpling die bore 172 in second curving die 94 to define a bore centrally over a body portion 186 of needle blank 100. Additionally, a portion of body portion 186 adjacent either end point 184 of needle blank 100 is exposed through notching channels 162 and 179 in first and second curving dies 78 and 94, respectively. Thus, as shown in FIG. 14A, upper dimpling die 136 and lower dimpling die rod 138 are positioned diametrically opposite and above a center portion of body portion 186 of needle blank 100.

Upper and lower dimpling dies 136 and 138 are sequenced so as to simultaneously impact body portion 186 of needle blank 100. Thus, referring now to FIGS. 15 and 15A, as upper base plate 16 comes down to a final or lower most position, lower dimpling die camming member 62, affixed to upper base plate 16, moves downwardly to drive lower dimpling die 74 upwardly into engagement with needle blank 100. Specifically, lower dimpling die camming member 62 engages upper camming edge 156 of transfer block 154 thereby driving transfer block 154 downwardly. As transfer block 154 is driven downwardly, transfer block camming surface 158 engages second camming surface 152 on drive member 144 to thereby force drive member 144 in a horizontal direction. As drive member 144 is driven horizontally, spring 148 is compressed between drive member 144 and lower base plate 18. As drive member 144 is moved horizontally, first camming surface 146 engages angled cam surface 196 on base member 140 to thereby drive lower dimpling die 74 upwardly. As lower dimpling die 74 is driven upwardly, spring 142 is compressed and lower dimpling die pin 138 is driven into engagement with needle blank 100. This occurs simultaneously with the lowering of notching and upper dimpling die 60.

Figures 15, 15A, 16:
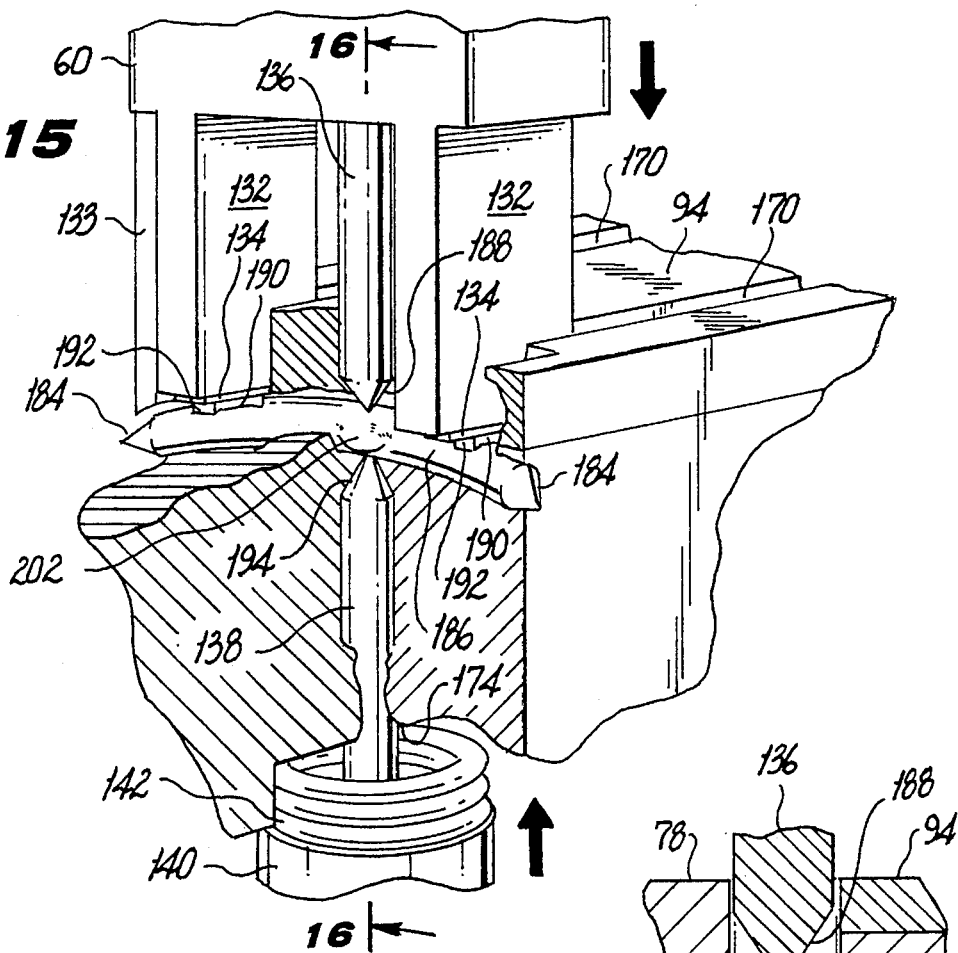
FIG. 15 is a enlarged perspective view, partially shown in section, illustrating the notching and dimpling die of the upper portion and lower portion dimpling die in engagement with the curved needle blank.
FIG. 15A is a partial side elevational view, partially shown in section, taken along the line 15A—15A of FIG. 14A and illustrating camming member positions for driving the lower portion dimpling die.
FIG. 16 is a partial cross-sectional view taken along the line 16—16 of FIG. 15 and illustrating deformation of the needle blank material due to the dimpling dies.

Thus, referring now to FIG. 15, as lower dimpling die pin 138 rises upwardly within channel 174, pin point 194 engages body portion 186 of needle blank 100. Simultaneously, as notching and upper dimpling dies 60 comes downwardly, point 188 of upper dimpling die 136 also engages body portion 186 of needle blank 100 at a position substantially diametrically opposite that engaged by point 194. Further, as notching and dimpling die 60 moves downwardly into engagement with needle blank 100, blades 132 drive notching dies 134, center die portion 190 and flared ends 192 into engagement with body portion 186 adjacent each end 184 to thereby impart apparatus engagement structure in the form of notches to one side of needle blank 100. As best appreciated from FIG. 15, notching dies 134 should be angled to conform to the curvature of the needle, so that the notches are formed perpendicular to the axis of the blank at the point they are formed. It has been found that about a 6° offset angle may be used.

As apparatus engagement structure or notches are imparted to body portion 186 of needle blank 100, points 184 may tend to deflect upwardly. Thus there may also be provided a point pusher 133 mounted adjacent blades 132 to hold points 184 down during the notching process.

Figure 18:
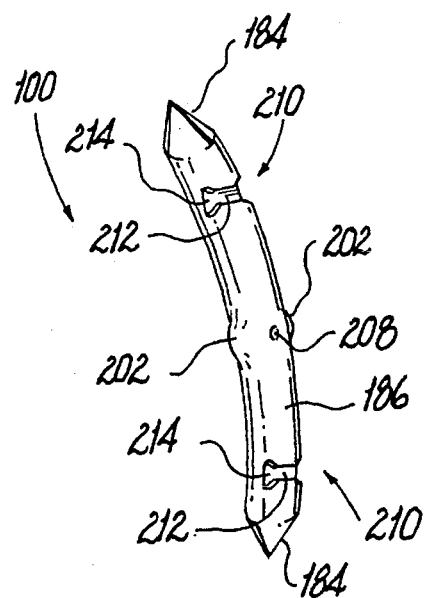
FIG. 18 is a perspective view of a surgical incision member formed on the apparatus of FIG. 1.
Figure 19:
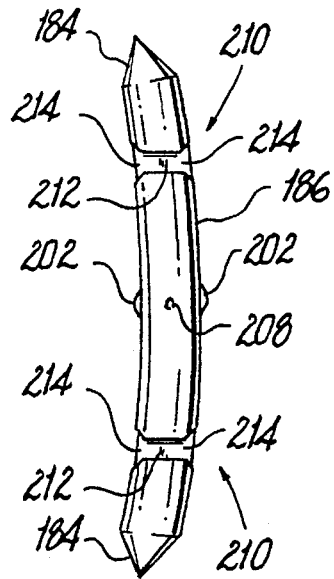
FIG. 19 is a plan view of the surgical incision member formed on the apparatus of FIG. 1.

Referring now to FIG. 16, as dimpling die points 188 and 194 of respective upper and lower dimpling dies 136, 138 engage body portion 186 of needle blank 100, needle stock material is forced outwardly into recesses 168 and 182 in curving dies 78 and 94, respectively. The displaced material forms the aforementioned crimping bulges, such as, for example, crimping bulges 202. Depending on needle size, recesses 168 and 182 preferably are dimensioned and configured to form bulges that project approximately 0.034 to 0.042 inches out of body portion 186, and, more preferably, approximately 0.039 inches. Further, points 194 and 188 impart diametrically opposite dimples or pilot holes in opposite sides of body portion 186 in needle blank 100. (FIGS. 18 and 19)

Figure 17:
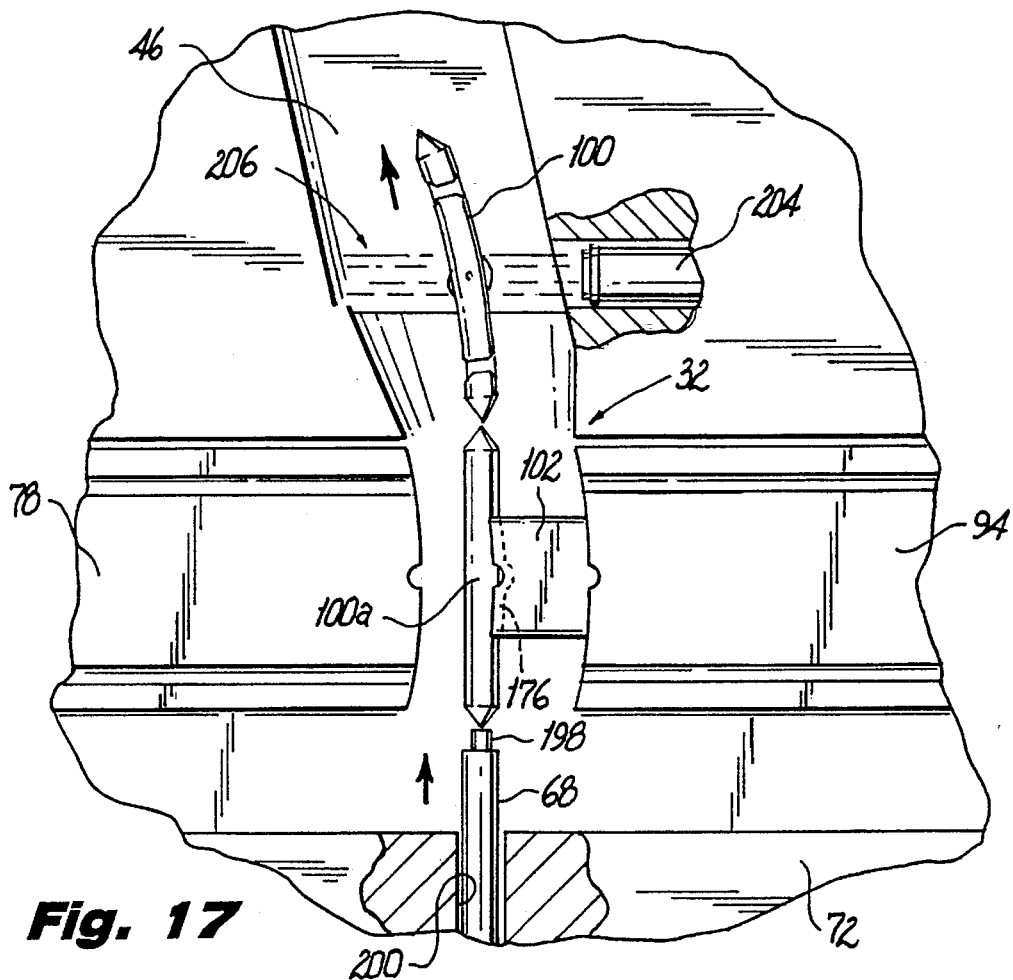
FIG. 17 is a top view, partially shown in section, illustrating the ejection of the curved, notched and dimpled surgical incision member and the insertion of a new, straight, double pointed, round bodied needle blank within the needle forming area.

Referring to FIG. 17, in conjunction with FIGS. 1 and 2, upon completion of a curving, notching and dimpling sequence, cylinders 20 are inflated to raise upper base plate 16 and thus camming members 48, 50 and notching and upper dimpling die 60 upwardly away from lower base plate 18. Thus, as camming members 48 and 50 and 62 clear respective blocks 86, 110 and 154, apparatus 10 is biased into an open and retracted position. Specifically spring 34 moves biasing rod 90 and thus cam block 86 away from the now formed surgical incision member 100. Similarly spring 36 drives biasing rod 114 and thus cam block 110 away from surgical incision member 100.

Notably, as cam block 110 is driven away from surgical incision member 100 thereby drawing with it second curving die 94, positioning finger 102, being spring biased by spring 104, remains in position in alignment with channel 200. Additionally as transfer block 154 is freed from movement, springs 150 and 142 move drive member 144 and lower dimpling die 74, respectively, away from surgical incision member 100.

The now formed surgical incision member surgical incision member 100 is directed to off load ramp 46 by, such as by providing an air current to assist in movement of the incision member blank. As fully formed surgical incision member 100 is ejected from needle forming area 32 an optical light sensor 204 creating a light screen 206, ensures that surgical incision member 100 passes therethrough and is fully ejected before apparatus 10 is recycled to insert a subsequent needle blank 100A into needle forming area 32.

Thus, should a formed surgical incision member 100 become stuck in a die, and not break through light screen 206, apparatus 10 is prevented from recycling and thereby prevent jamming of one needle blank against another. Once surgical incision member 100 has passed through light screen 206, apparatus 10 is free to recycle by causing push rod 68 to take a subsequent straight double pointed needle blank 100A and insert it into position between first and second curving dies 78 and 94 and within groove 176 in positioning finger 102. Thus, the cycle may be continually repeated to sequentially process a plurality of needle blanks 100.

FIGS. 18 and 19 illustrate a now curved and notched surgical incision member formed on apparatus 10 including a pair of dimples 208 formed by dimpling dies 136 and 138. Preferably, dimpling dies 136 and 138 impart a dimple having an angle of approximately 120° to facilitate subsequent hole drilling and to prevent burrs on opposite sides of the drilled hole. Additionally, the 120° angle of dimple 208 assists in preventing cutting of the edge of an suture crimped therein.

Further, needle blank 100 now includes apparatus engagement structure in the form of notches 210 each having a longitudinal central portion 212 for receipt of a suitable engagement structure, such as, for example, needle engaging members or blades of a surgical suturing apparatus. To facilitate engagement with the needle engagement members each notch 210 additionally includes end tapers 214 positioned on either side of central portion 212. Preferably the radius of curvature of forming surface 80 and 96 of first and second curving dies 78 and 94 respectively, correspond to the radius between a pivot point of a pair of arms or jaws and respective recesses in the arms or jaws for receipt of the surgical incision member.

At this point the surgical incision member may be taken to hole drilling equipment, such as, for example, laser or mechanical drilling equipment for drilling a suture attachment hole substantially in alignment with dimples 208. Further, a suture may be crimped or otherwise secured within the hole, in a manner described in U.S. patent application Ser. No. 08/260,579.

It will be understood that various modifications may be made to the embodiments disclosed herein. For example, and as noted above, die mechanisms may be provided to hold needle stock without curving to form straight surgical incision members for use with parallel jaw structure suturing apparatus. Further, various notching die configurations may be substituted to form apparatus engagement structure on the same, or even opposed, sides of a needle blank and engagable with various engagement structure on suturing apparatus. Additionally, various other needle blank configurations are contemplated for forming surgical incision members in the present apparatus, such as, for example, rectangular bodied needle blanks, needle blanks formed by curving around a mandrel and forming points by skiving or slicing the end portions, etc.

Therefore, the above description should not be construed as limiting, but merely as exemplifications as preferred embodiments. Those skilled in the art will envision other modifications within the scope and spirit of the claims appended hereto.

What is claimed is:

1. An apparatus for forming a surgical incision member comprising:

a) a first die mechanism including a pair of opposed surfaces, the pair of opposed surfaces including a convex surface and a concave surface which together define a groove therein and are configured to support a needle blank therebetween; and b) a notching die mounted for movement into and out of engagement with a needle blank positioned in the first die mechanism to impart at least one notch therein.

2. The apparatus according to claim 1, wherein the pair of opposed surfaces of the first die mechanism impart a predetermined curvature to the needle blank.

3. An apparatus for forming a surgical incision member comprising:

a) a first die mechanism including opposed surfaces forming a groove therein and configured to support a needle blank therebetween;

b) a notching die mounted for movement into and out of engagement with a needle blank positioned in the first die mechanism to impart at least one notch therein; and c) a dimpling die mounted for movement into and out of engagement with a needle blank positioned in the first die mechanism to impart at least one dimple therein.

4. The apparatus according to claim 3, wherein the notching die and the dimpling die are sequenced to notch and dimple the needle blank simultaneously.

5. An apparatus for forming a surgical incision member comprising:

a) a first die mechanism including opposed surfaces forming a groove therein and configured to support a needle blank therebetween; and b) a notching die separate from the first die mechanism and mounted for movement into and out of engagement with a needle blank positioned in the first die mechanism to impart at least one notch therein, wherein the first die mechanism includes a first holding member and a second holding member mounted for movement with respect to the first holding member to support a needle blank therebetween.

6. The apparatus according to claim 5, wherein the first holding member includes a slot intersecting a fast groove in the first holding member, the notching die being mounted for movement within the slot so as to engage the edge of the needle blank.

7. The apparatus according to claim 6, wherein the notching die has a pair of spaced apart die faces, the notching die movable adjacent the groove to bring the die faces into engagement with the edge of the needle blank.

8. The apparatus according to claim 7, further comprising a first dimpling die mounted intermediate the pair of die faces, the dimpling die engagable with the edge of the needle blank.

9. The apparatus according to claim 8, wherein the first dimpling die and pair of die faces are mounted for simultaneous engagement with an edge of the needle blank.

10. The apparatus according to claim 9, further comprising a second dimpling die mounted for movement with respect to the first dimpling die, the second dimpling die engagable with an edge of the needle blank.

11. The apparatus according to claim 10, wherein the second dimpling die is sequenced for simultaneous engagement with the fast dimpling die with the needle blank.

12. The apparatus according to claim 6, wherein the second needle holding member includes a second groove for receiving a portion of the needle blank therein, the second groove alignable with the first groove, when the first and second needle holding members are moved into adjacent relationship.

13. The apparatus according to claim 12, wherein the first and second grooves are configured to curve the needle blank held therebetween as the first and second needle holding members are moved into adjacent relationship.

14. The apparatus according to claim 13, wherein the notching die includes first and second spaced apart die faces, the first and second die faces movable within the channels to engage the needle blank.

15. The apparatus according to claim 14; further comprising a dimpling die intermediate the first and second die faces, the dimpling die movable within a bore defined between the first and second dies for engagement with the needle blank.

16. An apparatus for forming a surgical incision member comprising:
 a) a first die having a first groove therein for receipt of at least a portion of a needle blank;
 b) a second die mounted for movement between a position remote from the first die and a position adjacent the first die, the second die having a second groove alignable with the first groove to hold a needle blank therebetween, the first and second dies each having spaced apart channels intersecting the fast and second grooves; and
 c) a notching die mounted for movement within the channels so as to engage edges of the needle blank contained within the first and second grooves.

17. A method of forming a surgical incision member from straight needle stock comprising the steps of:
 a) holding a straight needle blank in a needle forming apparatus; and
 b) impacting at least one pair of complementary dies into a body portion of the needle blank so as to curve the needle blank by opposed complementary surfaces of the pair of dies, wherein the step of impacting includes the step of impacting the body portion to form at least one notch therein.

18. The method according to claim 17, wherein the step of impacting the body portion includes impacting the body portion at an intermediate portion to form at least one dimple therein.

19. The method of claim 18 wherein the step of impacting the body portion to form at least one dimple therein forms at least one bulge in a surface of the needle blank adjacent the at least one dimple.

20. The method of claim 18 wherein the step of impacting the body portion includes forming at least one bulge in a surface of the body portion.

* * * * *